United States Patent [19]
Castro et al.

[11] Patent Number: 6,114,038
[45] Date of Patent: Sep. 5, 2000

[54] FUNCTIONALIZED NANOCRYSTALS AND THEIR USE IN DETECTION SYSTEMS

[75] Inventors: Stephanie L. Castro, Columbus; Emilio Barberá-Guillem, Powell, both of Ohio

[73] Assignee: BioCrystal Ltd., Westerville, Ohio

[21] Appl. No.: 09/372,729

[22] Filed: Aug. 11, 1999

Related U.S. Application Data

[60] Provisional application No. 60/107,829, Nov. 10, 1998.

[51] Int. Cl.[7] .............................. A61K 49/00; B05D 7/00; B32B 9/00; B32B 9/04; H01L 29/04
[52] U.S. Cl. ...................... 428/402.24; 428/404; 257/65; 257/614; 257/642; 424/9.1; 424/9.32; 424/9.36; 424/9.42; 424/9.6; 427/213.3; 427/214; 427/215; 427/220
[58] Field of Search ............................... 428/402.24, 404; 257/65, 614, 642; 424/9.1, 9.32, 9.36, 9.42, 9.6; 427/213.3, 214, 215, 220

[56] References Cited

U.S. PATENT DOCUMENTS 5,751,018   5/1998   Alivisatos et al. ........................ 257/64

OTHER PUBLICATIONS

Bruchez et al., Semiconductor Nanocrystals as Fluorescent Biological Labels; Science, Sep. 25, 1998, vol. 281:2013–2015.

Chan and Nie, Quantum Dot Bioconjugates for Ultrasensitive Nonisotopic Detection; Science, Sep. 25, 1998, vol. 281:2016–2018.

Quantum Dots meet Biomolecules; Sep. 28, 1998; C&EN; p. 8.

*Primary Examiner*—Nathan M. Nutter
*Attorney, Agent, or Firm*—M. Bud Nelson

[57] ABSTRACT

Provided are compositions comprising water-soluble, functionalized nanocrystals. The water-soluble functionalized nanocrystals comprise quantum dots capped with a layer of a capping compound, and further comprise, by operably linking and in a successive manner, one or more additional compounds. The one or more additional compounds is comprised of at least a diaminocarboxylic acid which is operatively linked to the capping compound, and may further comprise an amino acid, an affinity ligand, or a combination thereof. Also provided are methods of using the functionalized nanocrystals having an affinity ligand to detect the presence or absence of a target substrate in a sample. The method comprises contacting the functionalized nanocrystals with the sample so that complexes are formed between the functionalized nanocrystals and substrate, if the substrate is present; exposing the complexes in the detection system to a wavelength of light suitable for exciting the functionalized nanocrystals of the complexes to emit a luminescence peak; and detecting the emitted luminescence peak.

47 Claims, 3 Drawing Sheets

FUNCTIONALIZED NANOCRYSTALS AND THEIR USE IN DETECTION SYSTEMS

This is a nonprovisional application based in part on earlier co-pending provisional application Ser. No. 60/107,829 filed Nov. 10, 1998, which is herein incorporated by reference.

FIELD OF INVENTION

This invention relates to novel compositions comprising functionalized nanocrystals. More particularly, the present invention relates to water-soluble nanocrystals which have a coat comprising a capping compound, and one or more additional compounds successively overlayered onto the capped nanocrystal. The present invention also relates to the use of the functionalized nanocrystals for providing a detectable signal in detection systems in which the nanocrystals are employed.

BACKGROUND OF THE INVENTION

Nonisotopic detection systems have become a preferred mode in scientific research and clinical diagnostics for the detection of biomolecules using various assays including flow cytometry, nucleic acid hybridization, DNA sequencing, nucleic acid amplification, immunoassays, histochemistry, and functional assays involving living cells. In particular, while fluorescent organic molecules such as fluoroscein and phycoerythrin are used frequently in detection systems, there are disadvantages in using these molecules in combination. For example, each type of fluorescent molecule typically requires excitation with photons of a different wavelength as compared to that required for another type of fluorescent molecule. However, even when a single light source is used to provide a single excitation wavelength (in view of the spectral line width), often there is insufficient spectral spacing between the emission optima of different fluorescent molecules to permit individual and quantitative detection without substantial spectral overlap. Further, currently available nonisotopic detection systems typically are limited in sensitivity due to the finite number of nonisotopic molecules which can be used to label a biomolecule to be detected.

Semiconductor nanocrystals ("quantum dots") are known in the art. Generally, quantum dots can be prepared which result in relative monodispersity (e.g., the diameter of the core varying approximately less than 10% between quantum dots in the preparation), as has been described previously (Bawendi et al., 1993, J. Am. Chem. Soc. 115:8706). Examples of quantum dots are known in the art to have a core selected from the group consisting of CdSe, CdS, and CdTe (collectively referred to as "CdX")(see, e.g., Norris et al., 1996, Physical Review B. 53:16338–16346; Nirmal et al., 1996, Nature 383:802–804; Empedocles et al., 1996, Physical Review Letters 77:3873–3876; Murray et al., 1996, Science 270: 1355–1338; Effros et al., 1996, Physical Review B. 54:4843–4856; Sacra et al., 1996, J. Chem. Phys. 103:5236–5245; Murakoshi et al., 1998, J. Colloid Interface Sci. 203:225–228; Optical Materials and Engineering News, 1995, Vol. 5, No. 12; and Murray et al., 1993, J. Am. Chem. Soc. 115:8706–8714; the disclosures of which are hereby incorporated by reference).

CdX quantum dots have been passivated with an inorganic coating ("shell") uniformly deposited thereon. Passivating the surface of the core quantum dot can result in an increase in the quantum yield of the luminescence emission, depending on the nature of the inorganic coating. The shell which is used to passivate the quantum dot is preferably comprised of YZ wherein Y is Cd or Zn, and Z is S, or Se. Quantum dots having a CdX core and a YZ shell have been described in the art (see, e.g., Danek et al., 1996, Chem. Mater. 8:173–179; Dabbousi et al., 1997, J. Phys. Chem. B 101:9463; Rodriguez-Viejo et al., 1997, Appl. Phys. Lett. 70:2132–2134; Peng et al., 1997, J. Am. Chem. Soc. 119:7019–7029; 1996, Phys. Review B. 53:16338–16346; the disclosures of which are hereby incorporated by reference). However, the above described quantum dots, passivated using an inorganic shell, have only been soluble in organic, non-polar (or weakly polar) solvents.

Figure 1A:
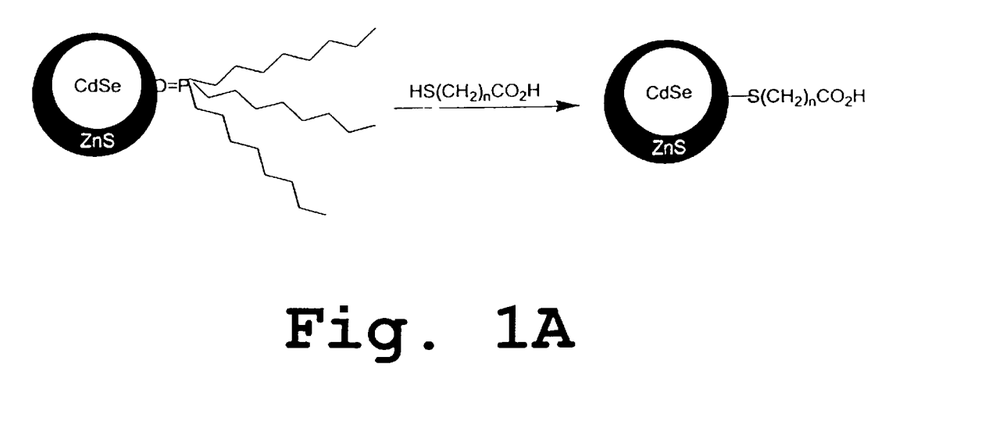
FIG. 1A is a schematic illustration showing exchange of the capping group of water-insoluble quantum dots with a large excess of neat mercaptocarboxylic acid.
Figure 1B:
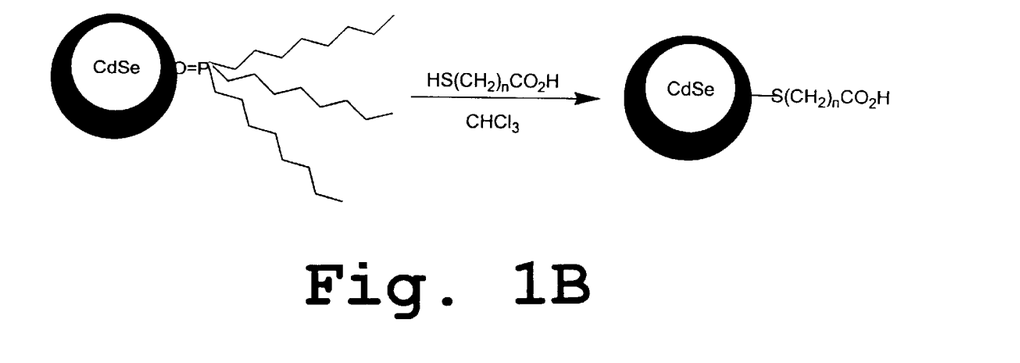
FIG. 1B is a schematic illustration showing exchange of the capping group of water-insoluble quantum dots with a large excess of mercaptocarboxylic acid in $CHCl_3$ solution.

To make quantum dots useful in biological applications, it is desirable that the quantum dots are water-soluble. "Water-soluble" is used herein to mean sufficiently soluble or suspendable in an aqueous-based solution, such as in water or water-based solutions or buffer solutions, including those used in biological or molecular detection systems as known by those skilled in the art. Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with a coating which will make the quantum dots water-soluble. For example, a mercaptocarboxylic acid may be used to exchange with the trialkylphosphine oxide coat. Exchange of the coating group is accomplished by treating the water-insoluble quantum dots with a large excess of neat mercaptocarboxylic acid (FIG. 1A). Alternatively, exchange of the coating group is accomplished by treating the water-insoluble quantum dots with a large excess of mercaptocarboxylic acid in $CHCl_3$ solution (FIG. 1B, Chan and Nie, 1998, Science 281:2016–2018). The thiol group of the new coating molecule forms Cd (or Zn)—S bonds, creating a coating which is not easily displaced in solution. Another method to make the CdX core/YZ shell quantum dots water-soluble is by the formation of a coating of silica around the dots (Bruchez, Jr. et al., 1998, Science 281:2013–2015). An extensively polymerized polysilane shell imparts water solubility to nanocrystalline materials, as well as allowing further chemical modifications of the silica surface. However, depending on the nature of the coating group, quantum dots which have been reported as water-soluble may have limited stability in an aqueous solution, particularly when exposed to air (oxygen) and/or light. More particularly, oxygen and light can cause the molecules comprising the coating to become oxidized, thereby forming disulfides which destabilize the attachment of the coating molecules to the shell. Thus, oxidation may cause the coating molecules to migrate away from the surface of the nanocrystals, thereby exposing the surface of the nanocrystals in resulting in "destabilized nanocrystals". Destabilized nanocrystals form aggregates when they interact together, and the formation of such aggregates eventually leads to irreversible flocculation of the nanocrystals.

Thus, there remains a need for a semiconductor nanocrystal which (a) is water-soluble; (b) is functionalized to enhance stability in aqueous solutions; (c) is a class of semiconductor nanocrystals that may be excited with a single wavelength of light resulting in detectable luminescence emissions of high quantum yield and with discrete luminescence peaks; and (d) is functionalized so as to be both water-soluble, and able to bind ligands, molecules, or probes of various types for use in an aqueous-based environment.

SUMMARY OF THE INVENTION

The present invention provides a composition comprising functionalized nanocrystals for use in non-isotopic detection systems. The composition comprises quantum dots (capped with a layer of a capping compound) that are water-soluble and functionalized by operably linking, in a successive manner, one or more additional compounds. In a preferred embodiment, the one or more additional compounds form successive layers over the nanocrystal. More particularly, the functionalized nanocrystals comprise quantum dots capped with the capping compound, and have at least a diaminocarboxylic acid which is operatively linked to the capping compound. Thus, the functionalized nanocrystals may have a first layer comprising the capping compound, and a second layer comprising a diaminocarboxylic acid; and may further comprise one or more successive layers including a layer of amino acid, a layer of affinity ligand, or multiple layers comprising a combination thereof. The composition comprises a class of quantum dots that can be excited with a single wavelength of light resulting in detectable luminescence emissions of high quantum yield and with discrete luminescence peaks.

In a method of detection of a target substrate using the functionalized nanocrystals according to the present invention, the functionalized quantum dots are further functionalized by binding an affinity ligand thereto. The resultant functionalized nanocrystal is placed in contact with a sample being analyzed for the presence or absence of a substrate for which the affinity ligand has binding specificity. Contact, and subsequent binding, between the affinity ligand of the functionalized nanocrystal and the substrate, if present in the sample, results in a complex comprising the functionalized nanocrystal-substrate which can emit a detectable signal for quantitation, visualization, or other form of detection.

The above and other objects, features, and advantages of the present invention will be apparent in the following Detailed Description of the Invention when read in conjunction with the accompanying drawings in which reference numerals denote the same or similar parts throughout the several illustrated views and embodiments.

DETAILED DESCRIPTION OF THE INVENTION

Definitions

By the term "substrate" is meant, for the purposes of the specification and claims to refer to a molecule of an organic or inorganic nature, the presence and/or quantity of which is being tested for; and which contains a molecular component (domain, sequence, epitope, portion, chemical group or determinant) for which the affinity ligand has binding specificity. The molecule may include, but is not limited to, a nucleic acid molecule, protein, glycoprotein, eukaryotic or prokaryotic cell, lipoprotein, peptide, carbohydrate, lipid, phospholipid, aminoglycan, chemical messenger, biological receptor, structural component, metabolic product, enzyme, antigen, drug, therapeutic, toxin, inorganic chemical, organic chemical, and the like. The substrate may be in vivo, in vitro, in situ, or ex vivo.

By the term "affinity ligand" is meant, for purposes of the specification and claims, to mean a molecule which has binding specificity and avidity for a molecular component of, or associated with, a substrate. In general, affinity ligands are known to those skilled in the art to include, but are not limited to, lectins or fragments (or derivatives) thereof which retain binding function; monoclonal antibodies ("mAb", including chimeric or genetically modified monoclonal antibodies (e.g., "humanized")); peptides; aptamers; nucleic acid molecules (including, but not limited to, single stranded RNA or single-stranded DNA, or single-stranded nucleic acid hybrids); avidin, or streptavidin, or avidin derivatives; and the like. The invention may be practiced using a preferred affinity ligand (e.g., a lectin) to the exclusion of affinity ligands other than the preferred affinity ligand. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include $F(ab')_2$, Fab', Fab, Fv, scFV, Fd' and Fd fragments. Methods for producing the various fragments or derivatives from mAbs are well known in the art (see, e.g., Pluckthum, 1992, Immunol. Rev. 130:152–188). For example, $F(ab')_2$ can be produced by pepsin digestion of the monoclonal antibody, and Fab' may be produced by reducing the disulfide bridges of $F(ab')_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. The construction of chimeric antibodies is now a straightforward procedure (Adair, 1992, Immunological Reviews 130: 5–40,) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, J. Immunol. 150:2844–2857). Methods for making a chimeric non-human/human mAb in general are described in detail in U.S. Pat. No. 5,736,137 (herein incorporated by reference). Aptamers can be made using methods described in U.S. Pat. No. 5,789,157 (herein incorporated by reference). Lectins, and fragments thereof, are commercially available. Lectins are known to those skilled in the art to include, but are not limited to, one or more of Aleuria aurantia lectin, Amaranthus caudatus lectin, Concanavalin A, Datura stramonium lectin, Dolichos biflorus agglutinin, soybean agglutinin, Erythrina cristagalli lectin, Galanthus nivalis lectin, Griffonia simplicifolia lectins, Jacalin, Macckia amurensis lectins, Maclura pomifera agglutinin, Phaeolepiota aurea lectins 1 and 2, Phaseolus vulgaris lectins, Ricin A, Moluccella laevis lectin, peanut agglutinin, Bauhinia purpurea agglutinin, Ricinus communis agglutinins, Sambucus nigra lectin, Vicia villosa agglutinin, Sophora japonica agglutinin, Caragana arborescens agglutinin, Helix aspersa agglutinin, Limax flavus lectin, limulin, wheat germ agglutinin, and Ulex europaeus agglutinin.

By the term "operably linked" is meant, for purposes of the specification and claims to refer to fusion or bond or an association of sufficient stability to withstand conditions encountered in a method of detection, between a combination of different molecules such as, but not limited to, between the quantum dot and a capping compound, between a capping compound and a diaminocarboxylic acid, between a diaminocarboxylic acid and a diaminocarboxylic acid, between a diaminocarboxylic acid and an affinity ligand, between a diaminocarboxylic acid and an amino acid, and between an amino acid and an affinity ligand, and a combination thereof. As known to those skilled in the art, and as will be more apparent by the following embodiments, there are several methods and compositions in which two or more molecules may be operably linked utilizing reactive functionalities. Reactive functionalities include, but are not limited to, bifunctional reagents/linker molecules, biotin, avidin, free chemical groups (e.g., thiol, or carboxyl, hydroxyl, amino, amine, sulfo, etc.), and reactive chemical groups (reactive with free chemical groups).

By the term "linker" is meant, for purposes of the specification and claims to refer to a compound or moiety that acts as a molecular bridge to operably link two different molecules, wherein one portion of the linker is operably linked to a first molecule, and wherein another portion of the linker is operably linked to a second molecule. The two different molecules may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers may include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. As illustrative examples, to operably link a hydroxyl group of a polynucleotide strand to an amino group of a diaminocarboxylic acid, the linker may have: a carboxyl group to form a bond with the polynucleotide, and a carboxyl group to form a bond with the diaminocarboxylic acid (see, e.g., U.S. Pat. Nos. 5,792,786, and 5,780,606 for various linkers known in the art). Heterobifunctional photoreactive linkers (e.g., phenylazides containing a cleavable disulfide bond) are known in the art. For example, a sulfosuccinimidyl-2-(p-azido salicylamido) ethyl-1,3'-dithiopropionate contains a N-hydroxy-succinimidyl group reactive with primary amino groups, and the phenylazide (upon photolysis) reacts with any amino acids. The linker may further comprise a protective group which blocks reactivity with a functional group on the linker which is used to react with and bind to a molecule to be linked. A deprotection reaction may involve contacting the linker to one or more conditions and/or reagents which removes the protective group, thereby exposing the functional group to interact with the molecule to be linked. Depending on the nature of the protective group, deprotection can be achieved by various methods known in the art, including, but not limited to photolysis, acidolysis, hydrolysis, and the like. Depending on such factors as the molecules to be linked, and the conditions in which the method of detection is performed, the linker may vary in length and composition for optimizing such properties as flexibility, stability, and resistance to certain chemical and/or temperature parameters. For example, short linkers of sufficient flexibility include, but are not limited to, linkers having from 2 to 10 carbon atoms (see, e.g., U.S. Pat. No. 5,817,795).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, and an amino acid precursor (e.g., citrulline and ornithine are intermediates in the synthesis of arginine). In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, and synthetic diaminocarboxylic acids such as 3,4-diaminobenzoic acid, 2,3-diaminopropionic acid, 2,4-diaminobutyric acid, 2,5-diaminopentanoic acid, and 2,6-diaminopimelic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, and homocysteine.

By the term "capping compound" is meant, for purposes of the specification and claims to refer to a compound having the formula $HS(CH_2)_nX$, wherein X is a carboxylate (carboxylic moiety). "n" is a number in the range of from 1 to about 20, and preferably greater than 4. The thiol group of the capping compound forms Cd (or Zn)—S bonds (depending on whether the shell is Cd or Zn), creating a layer which is not easily displaced in solution. This is an improvement over the use of a capping layer comprised of trialkylphosphine oxide ("TOPO"), in which a dative bond is formed between the oxide and the cadmium (or zinc); and which is readily displaced in the presence of other Lewis bases such as pyridine. Additionally, the carboxylic acid moiety of the capping compound imparts water solubility to the quantum dots. Exemplary capping compounds according to the present invention include, but are not limited to, mercaptocarboxylic acid, or mercaptofunctionalized amines (e.g., aminoethanethiol-HCl, homocysteine, or 1-amino-2-methyl-2-propanethiol-HCl).

The present invention provides compositions which can be used to generate a detectable signal comprising a light emission (e.g., luminescence emission) of high quantum yield, thereby considerably improving the sensitivity of a non-isotopic detection system. According to the present invention, functionalized nanocrystals comprise quantum dots (core and shell) which are functionalized by the addition of a first layer or coating comprising a capping compound (having the formula $HS(CH_2)_nX$, wherein X is a carboxylic moiety), and a second layer comprising a diaminocarboxylic acid. In another embodiment of the present invention, functionalized nanocrystals comprise quantum dots which are functionalized by the addition of a first layer comprising the capping compound, a second layer comprising a diaminocarboxylic acid, and a third layer comprising an affinity ligand. In another embodiment of the present invention, functionalized nanocrystals comprise quantum dots which are functionalized by the addition of a first layer comprising the capping compound, a second layer comprising a diaminocarboxylic acid, and a third layer comprising an amino acid. In yet another embodiment of the present invention, functionalized nanocrystals comprise quantum dots (core and shell) which are functionalized by the addition of a first layer or coating comprising the capping compound, a second layer comprising a diaminocarboxylic acid, a third layer comprising an amino acid, and a fourth layer comprising an affinity ligand. In each of the embodiments, the component of each successive layer is operably linked to the component of any contacting layer, as will be more apparent from the figures and following description.

In one embodiment of a method for using the functionalized nanocrystals according to the present invention, the functionalized nanocrystal comprises quantum dots which are functionalized by the addition of a first layer comprising the capping compound, a second layer comprising a diaminocarboxylic acid, and a third layer comprising an affinity ligand. The functionalized nanocrystals are first contacted with a sample under conditions suitable for the nanocrystals to contact and bind, via the affinity ligand portion, the substrate, if present, in the sample being analyzed for the presence or absence of the substrate. Alternatively, the functionalized nanocrystals may comprise quantum dots which are functionalized by the addition of a first layer comprising the capping compound, a second layer comprising a diaminocarboxylic acid, a third layer comprising an amino acid, and a fourth layer comprising an affinity ligand.

In another embodiment of a method for using the fucntionalized nanocrystals according to the present invention, the functionalized nanocrystals comprise quantum dots which are functionalized by the addition of a first layer comprising the capping compound, and a second layer comprising a diaminocarboxylic acid. The user may then operably link the desired affinity ligand to the second layer of the functionalized nanocrystal using methods known in the art. Alternatively, the functionalized nanocrystals may comprise quantum dots which are functionalized by the addition of a first layer comprising the capping compound, a second layer comprising a diaminocarboxylic acid, and a third layer comprising an amino acid; and the user may then operably link the desired affinity ligand to the third layer of the functionalized nanocrystal using methods known in the art.

EXAMPLE 1

In one embodiment, the composition according to the present invention comprises quantum dots which are functionalized by the addition of a layer comprising a capping compound having the formula $HS(CH_2)_nX$, (wherein X is a carboxylic moiety), and one or more successive layers comprising a diaminocarboxylic acid, an amino acid, or a combination thereof. Desirable features of the functionalized nanocrystals according to the present invention are that (a) can be excited with a single wavelength of light, (b) when excited, result in a detectable light emission (e.g., luminescence emission) of high quantum yield (e.g., a single quantum dot having at a fluorescence intensity greater than that of at least 10 rhodamine molecules), (c) have a light emission having a discrete luminescence peak, and (d) are water-soluble. The functionalized nanocrystals typically should have a substantially uniform size of less than 100 Angstroms, and preferably have a substantially uniform size in the range of sizes of from about 2 nm to about 10 nm (diameter). Preferred quantum dots used in the production of functionalized nanocrystals are comprised of a core of CdX wherein X is Se or Te or S. Such CdX quantum dots are passivated with an overlayering ("shell") uniformly deposited thereon, wherein the shell is preferably comprised of YZ wherein Y is Cd or Zn, and Z is S, or Se. The quantum dots, having a CdX core and a YZ shell, are functionalized so that the resultant nanocrystals are water-soluble. Also, as related to embodiments for in vivo detection systems, the functionalized nanocrystals are substantially non-toxic.

In this embodiment is illustrated the production of the functionalized nanocrystals. Exemplary quantum dots comprise a CdSe core, and a ZnS shell, "(CdSe)ZnS". TOPO capped CdSe were produced by placing TOPO (5 g) in a vessel, and dried at 150° C. for 1 hour under vacuum. The vessel was then backfilled with argon and heated to 300° C. In a controlled environment, $CdMe_2$ (7.2 μl, 0.1 mmol) and 1 M trioctylphosphine-Se solution (90 μl, 0.09 mmol) and trioctylphosphine (5 ml) were mixed, and then placed into an injector. This mixture was added to the TOPO in a reaction vessel, previously removed from the heat, in a single continuous injection with vigorous stirring, thereby resulting in the temperature decreasing to about 180° C. The reaction vessel was then subjected to heat to raise the temperature 5° C. every 10 minutes. Aliquots may be removed from the reaction vessel at various time intervals (5 to 10 minutes) to monitor the increase in size of nanocrystals over time, by the observation of the absorption spectra. The temperature may be changed, or the reaction halted, upon reaching nanocrystals of the desired characteristics. For example, the reaction vessel was cooled to about 60° C., 40 ml of methanol was added to cause the nanocrystals to flocculate. After centrifugation, a brightly colored liquid layer of nanocrystals dissolved in trioctylphosphine remained. The methanol/TOPO layer was decanted off, and pyridine (10 ml) was added to the nanocrystal solution and allowed to stand for at least one hour. The nanocrystals were then precipitated as a powder by addition of hexanes, and separated by centrifugation. The powder was washed once more with hexanes, then dissolved in 30 ml pyridine, and centrifuged to remove any reaction byproducts.

To prepare (CdSe)ZnS nanocrystals, the pyridine solution (30 ml) was placed in a reaction vessel, rigorously degassed with an inert gas (e.g., argon), and refluxed for one hour before adjusting the temperature to approximately 100° C. Equimolar amounts of diethyl zinc (zinc source) and hexamethyldisilathiane (sulfide source) were dissolved in trioctylphosphine (2–4 ml) in a controlled environment (glove box) and loaded into an injector. A reaction vessel containing the CdSe dots dispersed in pyridine was heated under an atmosphere of argon, and the Zn and S were added dropwise, via the injector, with vigorous stirring of the mixture for 5–10 minutes. The mixture was left stirring for several hours. After cooling, the pyridine solution was centrifuged to remove any insoluble material. The overcoated nanocrystals were stored in this solution to ensure that the surface of the nanocrystals remained passivated with pyridine.

To prepare nanocrystals which are water soluble, the pyridine overcoating of the (CdX) core/YZ shell nanocrystals were exchanged with a capping compound which contributes to the water-solubility of the resultant nanocrystals. For example, a capping compound comprising mercaptocarboxylic acid may be used to exchange with the pyridine overcoat. Exchange of the coating group is accomplished by treating the water-insoluble, pyridine-capped quantum dots with a large excess of neat mercaptocarboxylic acid (FIG. 1A). To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. The solution is allowed to stand at room temperature for at least six hours. Longer incubation times lead to increased substitution by the thiol. Overnight incubations are ideal. Chloroform is added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with the capping compound, were then soluble in water or other aqueous solutions. The nanocrystals, in an aqueous solution, were centrifuged once more, filtered through a 0.2 μm filter, degassed with argon, and stored in an amber vial. Failure to protect the nanocrystals, in solution, from air and light leads to irreversible flocculation, usually within a week. Although proper storage conditions can extend the shelf life of these water-soluble nanocrystals to several months, there is a drawback because of their sensitivity to oxidation, and a need for repeatedly de-gassing the vial after each use. As mentioned previously, oxidation may result in the capping compound becoming destabilized (e.g., individual molecules of the capping compound form disulfides, and lose contact with the shell of the nanocrystal); and destabilization can result in irreversible flocculation of the nanocrystals.

Thus, single-site attachment of the capping compound (a mercaptocarboxylic acid; e.g., mercaptoacetic acid, mercaptopropionic acid, mercaptoundecanoic acid, etc.) suffers from limited stability in aqueous solution in the presence of water when exposed to air (oxygen) and light. To improve solubility and stability of the nanocrystals capped with the capping compound, the nanocrystals were overlayered with an organic molecule comprising a diaminocarboxylic acid in forming a functionalized nanocrystal. In a preferred embodiment, the diaminocarboxylic acid (a) contributes to the water-solubility of the functionalized nanocrystal because it has polar functional groups which can hydrogen-bond with water; (b) has at least two free functional groups which are carboxyl-reactive, thereby enabling the diaminocarboxylic acid molecule to operably link to and crosslink carboxyl groups extending from the capping compound on the capped nanocrystals; and (c) once operably linked to the capping compound, has one or more free functional groups which can be used for operably linking an affinity ligand thereto. Regarding stability, cross-linking may hinder the destabilization of single molecules of the capping compound operably linked to the nanocrystals. For example, if two molecules of the capping compound become operably linked to a diaminocarboxylic acid, and if one of the two molecules of the capping compound becomes destabilized, the destabilized molecule may be held into place (close proximity and in association) with respect to the shell of the nanocrystal via the other molecule of the capping compound which is operably linked, and cross-linked, to the diaminocarboxylic acid. Additionally, each successive layer of diaminocarboxylic acid (and/or amino acid, and/or affinity ligand) may further protect the capping compound from oxidation by light and/or air. A single diaminocarboxylic acid molecule has two free amino groups (carboxyl reactive groups) which can operably link to two carboxylic acid groups on the capping compound coating the nanocrystals via the formation of amide bonds. Amide bonds form the backbone of peptide chains, are thermodynamically stable, and may irreversibly cross link the capping compound (e.g., the mercaptoacetic acid coat). Additionally, a free carboxylic acid group on the diaminocarboxylic acid will remain as a site for attachment (operably linking) of other molecules to the diaminocarboxylic acid layer. In a more preferred embodiment, the diaminocarboxylic acid comprises lysine (2,6-diaminohexanoic acid).

Figure 2:
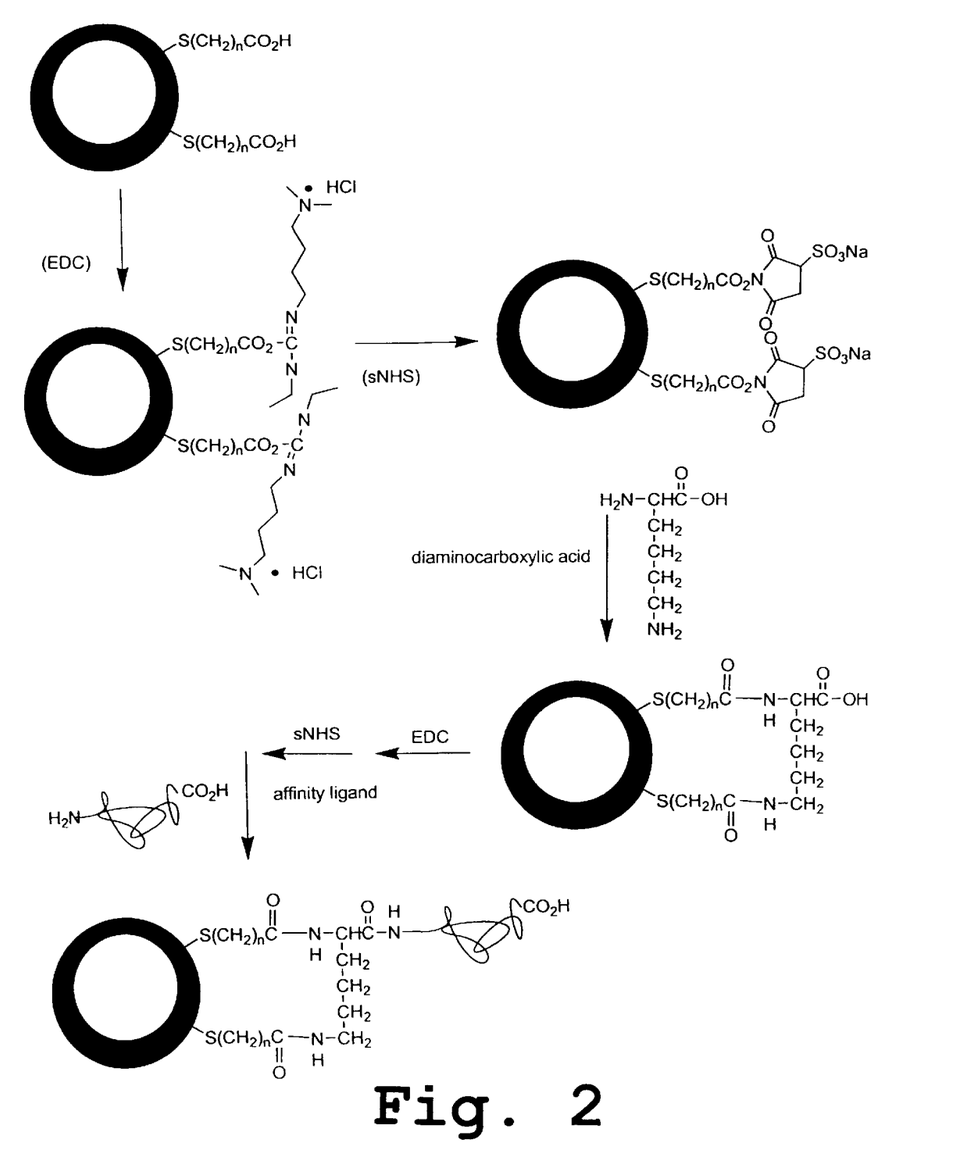
FIG. 2 is a schematic illustrating chemically modifying a water-soluble quantum containing a layer of a capping compound to further comprise a layer of a diaminocarboxylic acid, and a layer of an affinity ligand (e.g., avidin).

For operably linking diaminocarboxylic acid to the capping compound of capped nanocrystals, commercially available crosslinking agents and methods known to those skilled in the art may be used. For example, and as illustrated in FIG. 2, mercaptoacetic acid-capped nanocrystals were dissolved in an aqueous buffer system (pH of about 7). The buffer may comprise such buffers as PBS or HEPES. It is noted that the presence of phosphate has been shown to dramatically decrease the lifetime of the crosslinking agent from hours to minutes. To the capped nanocrystals was added EDC (1-ethyl-3-[3-dimethylaminopropyl] carbdiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration and stirred for 15 minutes. The entire solution was then added dropwise, with stirring, to a solution of lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, functionalized nanocrystals can be solubilized in an aqueous solution of choice. Once solubilized, the resulting solution can be stored in an amber vial under an inert gas to prevent flocculation.

In another embodiment, as also illustrated in FIG. 2, the functionalized nanocrystals comprised of a first layer comprising the capping compound and a second layer comprising a diaminocarboxylic acid, is further functionalized by the addition of an affinity ligand. As an illustrative example, a protein (glycoprotein, peptide, lipoprotein, etc.) having a free carboxyl-reactive group (e.g., an amine group) can be operably linked to the free carboxyl group of the diaminocarboxylic acid of the functionalized nanocrystals using methods known in the art. For example, an affinity ligand selected from the group consisting of avidin, a monoclonal antibody, an F'ab fragment, or a lectin (e.g., wheat germ agglutinin) may be operably linked using EDC and sulfo-NHS using the general methods as previously described herein. More particularly, EDC functions to activate at least one reactive functionality (e.g., a carboxylate) to catalyze its reaction with another reactive functionality such as the amine group of a protein. The functionalized nanocrystals (1 ml, $8.1 \times 10^{-9}$ mol) were esterified by treatment with EDC ($8.1 \times 10^{-6}$ mol), followed by treatment with sulfo-NHS ($8.9 \times 10^{-6}$ mol) at ambient temperature in buffered aqueous solution (at about pH 7.4) for 30 minutes. 2-mercaptoethanol was added to the solution at a concentration of 20 mM, and the mixture was stirred for 15 minutes to quench any unreacted EDC. Using a lectin wheat germ agglutinin (WGA) as an exemplary affinity ligand, the nanocrystals were then contacted with WGA ($8.1 \times 10^{-9}$ mol in PBS, 1 mg/ml) with vigorous stirring, and the reaction mixture was stirred for 2 hours (e.g., conditions sufficient to form an amide bond between the EDC-activated carboxylates of the diaminocarboxylate layer and the amine groups on WGA in forming functionalized nanocrystals which are water-soluble and have lectin operably linked thereto). Ethanolamine was added at a concentration of 30 mM to quench the coupling reaction, and the reaction mixture was stirred for 30 minutes. The resulting solution was then filtered through a 30 kD molecular weight cutoff centrifugal filter to remove excess reagents. The concentrated material was then diluted to 1 ml in buffer (e.g., PBS) or other suitable aqueous solution. Essentially, the same procedure can be used to operably link avidin, an antibody, or other affinity ligand having at least one free carboxyl-reactive group.

In illustrating an embodiment of a method of using the functionalized nanocrystals, it may be desirable to attach a plurality of oligonucleotides to the functionalized nanocrystals for subsequent use in a nucleic acid probe hybridization detection system. In one illustration of this embodiment, the functionalized nanocrystals comprise avidinylated, functionalized nanocrystals (e.g., (CdX) core/YZ shell, capped with the capping compound, layered with a diaminocarboxylic acid with operably linking to the cappping compound, layered with avidin with operably linking to the diaminocarboxylic acid) which are then contacted with, and operably linked to, a plurality of molecules of the desired oligonucleotide, each of which contains one or more biotin molecules (including native biotin or a biotin derivative having avidin-binding activity; e.g., biotin dimers, biotin multimers, carbo-biotin, and the like). Preferably, the oligonucleotides are biotinylated at a single terminus of the strand. Using methods known to those skilled in the art, biotin molecules can be added to or incorporated in a nucleotide strand, and even localized to one terminus, such as by directing synthesis of the nucleotide strands with nucleotides and biotin-nucleotides, or by biotinylating the 5' aminogroup of the nucleotide with sulfo-NHS-biotin. Thus, by contacting avidinylated, functionalized nanocrystals with biotinylated oligonucleotides, formed is a functionalized nanocrystal having a plurality of oligonucleotides extending therefrom (e.g., through the biotinavidin binding, the plurality of oligonucleotides become operably linked to the functionalized nanocrystals). These functionalized nanocrystals may then be used as probes in a nucleic acid probe hybridization detection system using standard methods known to those skilled in the art.

EXAMPLE 2

Figure 3:
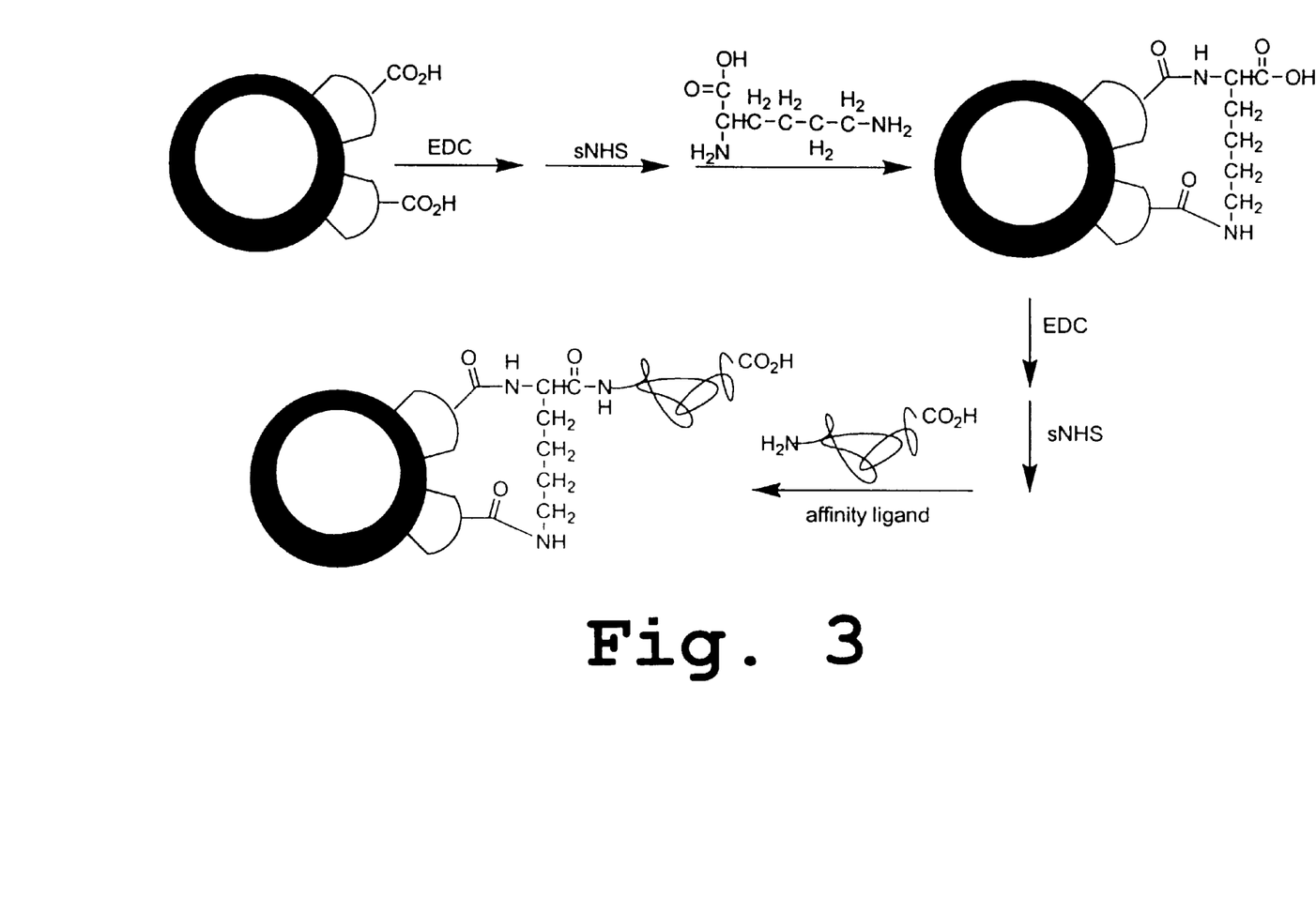
FIG. 3 is a schematic illustrating chemically modifying a water soluble quantum dot containing a layer of a capping compound to further comprise a layer of a diaminocarboxylic acid, an additional layer of a diaminocarboxylic acid, and a layer of an affinity ligand.

In another embodiment of the functionalized nanocrystals according to the present invention, the functionalized nanocrystals comprise quantum dots functionalized by the addition of a first layer comprising the capping compound, a second layer comprising a diaminocarboxylic acid, and a third layer comprising an amino acid. Functionalized nanocrystals comprising the addition of a first layer comprising the capping compound, a second layer comprising a diaminocarboxylic acid may be produced using the methods outlined in Example 1, and FIG. 2 herein. These functionalized nanocrystals are further functionalized by the addition of another layer comprising an amino acid, such as illustrated in FIG. 3. FIG. 3 illustrates the addition of an additional layer of an amino acid wherein the amino acid comprises a diaminocarboxylic acid. In this illustration, the diaminocarboxylic acid molecules of the third layer can operably link, and crosslink, the free carboxyl groups of the diaminocarboxylic acid molecules of the second layer. Thus, not only does the diaminocarboxylic acid molecules of the third layer contribute to solubility, but may also contribute to further stability to the functionalized nanocrystal (e.g., by adding some protection against oxidation). However, it is also noted that with each diaminocarboxylic acid layer added, the number of free functional groups for reaction to operably link with a subsequent carboxylic acid layer or affinity ligand is reduced. If, for example, an affinity ligand is to be operably coupled to the diaminocarboxylic acid molecules of the third layer, a reduction in the number of free functional groups for reaction with the affinity ligand may be desirable, particularly if it is desired to operably link relatively fewer molecules of the affinity ligand to the functionalized nanocrystals (e.g., because of one or more of the size, chemical characteristics, and specificity of the affinity ligand, or substrate to which the affinity lignd binds). However, if a maximum number of affinity ligands is desired to be operably linked to the functionalized nanocrystals, it may be disadvantageous to use a third layer comprising an amino acid comprising a diaminocarboxylic acid. If a maximum number of affinity ligands is desirable, alternative embodiments include: (a) operably linking the affinity ligand to functionalized nanocrystals comprising a first layer comprising the capping compound, and a second layer comprising a diaminocarboxylic acid; or (b) operably linking a third layer (comprising an amino acid comprising a monoaminocarboxylic acid) to the second layer comprising the diaminocarboxylic acid, and then operably link the affinity ligand to the functionalized nanocrystals via the free carboxyl group of the monoaminocarboxylic acid. Thus, various factors, such as the nature of the affinity ligand to be operably linked, may guide the choice of a carboxylic acid for a third layer in further functionalizing the nanocrystals according to the present invention.

As illustrated in FIG. 3, functionalized nanocrystals comprising the addition of a first layer comprising the capping compound, and a second layer comprising a diaminocarboxylic acid, are mixed with EDC and sulfo-NHS in 500–1000 times excess. The resulting solution is stirred at room temperature for 30 minutes. Mercaptoethanol is added to neutralize unreacted EDC at 20 mM concentration and stirred for 15 minutes. The entire solution is then added dropwise, with stirring, to a solution of an amino acid comprising a diaminocarboxylic acid (e.g., lysine in large excess) in the same buffer; and the mixture is stirred for 2 hours at room temperature. Ethanolamine (30 mM) is added to quench the reaction; and the mixture is stirred for 30 minutes at room temperature or left overnight at 4° C. The solution is centrifuged to remove and precipitate solids, and then ultrafiltered through a 30 kD MW centrifugal filter. The resultant concentrated, functionalized nanocrystals can be solubilized in an aqueous solution of choice. Once solubilized, the resulting solution can be stored in an amber vial under an inert gas to prevent flocculation. This process can also be used to add a third layer comprising an amino acid comprising a monoaminocarboxylic acid rather than a diaminocarboxylic acid. In either case, functionalized nanocrystals comprising a third layer comprising an amino acid may be further functionalized by operably linking an affinity ligand to the free amine reactive group(s) (or other free reactive groups) of the amino acid comprising the third layer using methods previously described herein.

EXAMPLE 3

In a method of detection of a target substrate using the functionalized nanocrystals according to the present invention, the functionalized nanocrystals are placed in contact with a sample being analyzed for the presence or absence of a substrate for which the affinity ligand of the functionalized nanocrystals has binding specificity. Contact, and subsequent binding, between the affinity ligand of the functionalized nanocrystal and the substrate, if present in the sample, in a detection system results in complexes comprising the functionalized nanocrystal-substrate which can emit a detectable signal for quantitation, visualization, or other form of detection. Upon formation of the complexes comprising the functionalized nanocrystal-substrate, the detectable signal emitted therefrom may be detected by first exposing the complexes formed in the detection system to a wavelength of light (visible, or UV, or a combination thereof) that is suitable for exciting the functionalized nanocrystals to emit a luminescence peak. The peak is then detected, or detected and quantitated, by appropriate detection means (e.g., photodetector, filters, fluorescence microscope, and the like). Quantitation of the amount of substrate present is directly related to the intensity of the emitted luminescence peak. As known to those skilled in the art of nanocrystals, the absorbance peak and fluorescence peak emissions depend on such factors which include, but are not limited to, the chemical nature, and size, of the functionalized nanocrystals. For example, functionalized CdSe/ZnS nanocrystals having a substantially uniform size comprising a diameter of about 68.4 angstroms (A) may be excited with light of a wavelength in the range of from about 400 nm to 500 nm, and emit a luminescence peak (orange) at 609 nm which may be detected using appropriate detection means. Functionalized CdSe/ZnS nanocrystals having a substantially uniform size comprising a diameter of about 53.2 A may be excited with light of a wavelength in the range of from about 400 nm to 500 nm, and emit a luminescence peak (yellow) at 545 nm which may be detected using appropriate detection means. Functionalized CdSe/ZnS nanocrystals having a substantially uniform size comprising a diameter of about 46.6 A may be excited with light of a wavelength in the range of from about 400 nm to 500 nm, and emit a luminescence peak (green) at 522 nm which may be detected using appropriate detection means. Detection may be by detection means comprising a scanner or reader or other analytical instrument which can detect luminescence peaks in the range of about 450 nm to about 700 nm; and, optionally (when more than one color is used in the detection system), distinguish between discrete luminescence peaks within that range. In the class of nanocrystals used in the present invention, many sizes of which can be excited with a single wavelength of light, resulting in many emissions of colors that can be detected simultaneously and distinctly. Thus, for example, it will be apparent to those skilled in the art that more than one target substrate may be detected in a detection system simultaneously by using more than one uniform size of functionalized nanocrystals; with each uniform size having an affinity ligand operably linked thereto which has a different binding specificity (hence can detect a different target substrate) than the affinity ligand operably linked to functionalized nanocrystals of a different uniform size. As will be apparent to one skilled in the art, the detection system may include, but is not limited to, one or more of an affinity assay (e.g, immunoassay such as an ELISA), fluorescent staining (e.g., immunofluorescent staining on a glass slide), flow cytometry, nucleic acid sequencing, nucleic acid hybridization, nucleic acid synthesis or amplification, identification verification (e.g., identification card or bank card), molecular sorting (e.g., cell sorting by flow cytometry), and the like.

In one illustration of this embodiment, functionalized nanocrystals comprising a core, a shell, a capping compound comprising the formula $HS(CH_2)_nX$ wherein X is a carboxylate, a diaminocarboxylic acid which is operably linked to the capping compound, and WGA which is operably linked to the diaminocarboxylic acid, is produced using the methods outlined herein in Example 1 ("WGA-labeled, functionalized nanocrystals). To a tube containing approximately 70,000 cells of Met-129 cancer cell line (chemically induced murine mammary carcinoma) was added 200 μl of the WGA-labeled, functionalized nanocrystals, and the mixture was then rotated gently on a platform mixer. Met-129 cells have one or more cell surface glycoproteins with either terminal N-acetylglucosamine residues or with terminal sialic acid residues (e.g., mucin) which may be reactive with WGA. After 10 minutes, a drop of the mixture was placed on a microscope slide, and covered with a coverslip. Examination of the sample with a fluorescence microscope revealed that the Met-129 cells aggregated together, with the outlines of the cells clearly visible by fluorescent staining with the WGA-labeled, functionalized nanocrystals. There was very little background fluorescence remaining in the reaction media. After 30 minutes, another sample was examined, and again at 2 hours. Both of the latter samples showed agglutination of the cells, with fluorescent staining of the outside cell walls by the WGA-labeled, functionalized nanocrystals.

As a negative control for the staining mediated by the WGA-labeled, functionalized nanocrystals, unlabeled functionalized nanocrystals were added to a tube containing Met-129 cells. At 10 minutes and 30 minutes, a low level of non-specific staining of cells was observed, but the cells were spatially isolated from each other and were not forming aggregates. At two hours, some non-specific staining was also observed, as well as some aggregation of the cells. In a positive control reaction, WGA-labeled with Oregon Green fluorescent dye was added to a tube containing Met-129 cells. At each sample time, the cells were observed as large, brightly stained aggregates. However, the cell media retained a high level of background fluorescence.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A water-soluble, functionalized nanocrystal comprising: a quantum dot having a core and a shell; a capping compound operably linked to the quantum dot, wherein the capping compound comprises a compound having the formula $HS(CH_2)_nX$, wherein X is a carboxylate; and a diaminocarboxylic acid which is operably linked to the capping compound.

2. The water-soluble, functionalized nanocrystal according to claim 1, wherein the core comprises CdX, and wherein X is Se, Te or S.

3. The water-soluble, functionalized nanocrystal according to claim 1, wherein the shell comprises YZ, and wherein Y is Cd or Zn, and Z is S, or Se.

4. The water-soluble, functionalized nanocrystal according to claim 1, wherein the capping compound is selected from the group consisting of a mercaptocarboxylic acid, a mercaptofunctionalized amine, aminoethanethiol-HCl, homocysteine, and 1-amino-2-methyl-2-propanethiol-HCl.

5. The water-soluble, functionalized nanocrystal according to claim 1, wherein the diaminocarboxylic acid forms a layer over the capping compound.

6. The water-soluble, functionalized nanocrystal according to claim 1, wherein an d the diaminocarboxylic acid is selected from the group consisting of lysine, asparagine, glutamine, arginine, citrulline, ornithine, 5-hydroxylysine, djenkolic acid, β-cyanoalanine, 3,4-diaminobenzoic acid, 2,3-diaminopropionic acid, 2,4-diaminobutyric acid, 2,5-diaminopentanoic acid, and 2,6-diaminopimelic acid.

7. The water-soluble, functionalized nanocrystal according to claim 1, further comprising an affinity ligand which is operably linked to the diaminocarboxylic acid.

8. The water-soluble, functionalized nanocrystal according to claim 7, wherein the affinity ligand forms a layer over the diaminocarboxylic acid.

9. The water-soluble, functionalized nanocrystal according to claim 7, wherein the affinity ligand is selected from the group consisting of a lectin, a monoclonal antibody, a peptide, an aptamer, a nucleic acid molecule, avidin, streptavidin, and an avidin derivative.

10. A water-soluble, functionalized nanocrystal comprising: a quantum dot having a core and a shell; a capping compound operably linked to the quantum dot, wherein the capping compound comprises a compound having the formula $HS(CH_2)_nX$, wherein X is a carboxylate; a diaminocarboxylic acid which is operably linked to the capping compound; and an amino acid which is operably linked to the diaminocarboxylic acid.

11. The water-soluble, functionalized nanocrystal according to claim 10, wherein the core comprises CdX, and wherein X is Se, Te or S.

12. The water-soluble, functionalized nanocrystal according to claim 10, wherein the shell comprises YZ, and wherein Y is Cd or Zn, and Z is S, or Se.

13. The water-soluble, functionalized nanocrystal according to claim 10, wherein the capping compound is selected from the group consisting of a mercaptocarboxylic acid, a mercaptofunctionalized amine, aminoethanethiol-HCl, homocysteine, and 1-amino-2-methyl-2-propanethiol-HCl.

14. The water-soluble, functionalized nanocrystal according to claim 10, wherein the amino acid forms a layer over the diaminocarboxylic acid.

15. The water-soluble, functionalized nanocrystal according to claim 10, wherein the amino acid is selected from the group consisting of a monocarboxylic acid and a diaminocarboxylic acid.

16. The water-soluble, functionalized nanocrystal according to claim 15, wherein the amino acid comprises a diaminocarboxylic acid, and the diaminocarboxylic acid is selected from the group consisting of lysine, asparagine, glutamine, arginine, citrulline, ornithine, 5-hydroxylysine, djenkolic acid, β-cyanoalanine, 3,4-diaminobenzoic acid, 2,3-diaminopropionic acid, 2,4-diaminobutyric acid, 2,5-diaminopentanoic acid, and 2,6-diaminopimelic acid.

17. The water-soluble, functionalized nanocrystal according to claim 15, wherein the amino acid comprises a monoaminocarboxylic acid, and the monoaminocarboxylic acid is selected from the group consisting of glycine, serine, threonine, cysteine, β-alanine, homoserine, γ-aminobutyric acid, and homocysteine.

18. The water-soluble, functionalized nanocrystal according to claim 10, further comprising an affinity ligand which is operably linked to the amino acid.

19. The water-soluble, functionalized nanocrystal according to claim 18, wherein the affinity ligand forms a layer over the diaminocarboxylic acid.

20. The water-soluble, functionalized nanocrystal according to claim 18, wherein the affinity ligand is selected from the group consisting of a lectin, a monoclonal antibody, a peptide, an aptamer, a nucleic acid molecule, avidin, streptavidin, and an avidin derivative.

21. A water-soluble, functionalized nanocrystal comprising:
(a) a quantum dot having a core wherein the core comprises CdX, and wherein X is Se, Te or S;
(b) a shell, wherein the shell comprises YZ, and wherein Y is Cd or Zn, and Z is S, or Se;
(c) a capping compound operably linked to the quantum dot, wherein the capping compound comprises a compound having the formula $HS(CH_2)_nX$, and wherein X is a carboxylate; and
(d) a diaminocarboxylic acid which is operably linked to the capping compound.

22. The water-soluble, functionalized nanocrystal according to claim 21, wherein the capping compound is selected from the group consisting of a mercaptocarboxylic acid, a mercaptofunctionalized amine, aminoethanethiol-HCl, homocysteine, and 1-amino-2-methyl-2-propanethiol-HCl.

23. The water-soluble, functionalized nanocrystal according to claim 21, wherein the diaminocarboxylic acid forms a layer over the capping compound.

24. The water-soluble, functionalized nanocrystal according to claim 21, wherein and the diaminocarboxylic acid is selected from the group consisting of lysine, asparagine, glutamine, arginine, citrulline, ornithine, 5-hydroxylysine, djenkolic acid, β-cyanoalanine, 3,4-diaminobenzoic acid, 2,3-diaminopropionic acid, 2,4-diaminobutyric acid, 2,5-diaminopentanoic acid, and 2,6-diaminopimelic acid.

25. The water-soluble, functionalized nanocrystal according to claim 21, further comprising an affinity ligand which is operably linked to the diaminocarboxylic acid.

26. The water-soluble, functionalized nanocrystal according to claim 25, wherein the affinity ligand forms a layer over the diaminocarboxylic acid.

27. The water-soluble, functionalized nanocrystal according to claim 25, wherein the affinity ligand is selected from the group consisting of a lectin, a monoclonal antibody, a peptide, an aptamer, a nucleic acid molecule, avidin, streptavidin, and an avidin derivative.

28. The water-soluble, functionalized nanocrystal according to claim 21, further comprising an amino acid which is operably linked to the diaminocarboxylic acid.

29. The water-soluble, functionalized nanocrystal according to claim 28, wherein the amino acid forms a layer over the diaminocarboxylic acid.

30. The water-soluble, functionalized nanocrystal according to claim 28, wherein the amino acid is selected from the group consisting of a monocarboxylic acid and a diaminocarboxylic acid.

31. The water-soluble, functionalized nanocrystal according to claim 30, wherein the amino acid comprises a diaminocarboxylic acid, and the diaminocarboxylic acid is selected from the group consisting of lysine, asparagine, glutamine, arginine, citrulline, ornithine, 5-hydroxylysine, djenkolic acid, β-cyanoalanine, 3,4-diaminobenzoic acid, 2,3-diaminopropionic acid, 2,4-diaminobutyric acid, 2,5-diaminopentanoic acid, and 2,6-diaminopimelic acid.

32. The water-soluble, functionalized nanocrystal according to claim 30, wherein the amino acid comprises a monoaminocarboxylic acid, and the monoaminocarboxylic acid is selected from the group consisting of glycine, serine, threonine, cysteine, β-alanine, homoserine, γ-aminobutyric acid, and homocysteine.

33. The water-soluble, functionalized nanocrystal according to claim 28, further comprising an affinity ligand which is operably linked to the amino acid.

34. The water-soluble, functionalized nanocrystal according to claim 33, wherein the affinity ligand forms a layer over the amino acid.

35. The water-soluble, functionalized nanocrystal according to claim 33, wherein the affinity ligand is selected from the group consisting of a lectin, a monoclonal antibody, a peptide, an aptamer, a nucleic acid molecule, avidin, streptavidin, and an avidin derivative.

36. A method of using the water-soluble, functionalized nanocrystal according to claim 7 in a detection system, the method comprising the steps of:

(a) contacting the functionalized nanocrystals with a sample being analyzed for the presence or absence of a substrate for which the affinity ligand has binding specificity, wherein if the substrate is present in the sample, formed are complexes comprising the functionalized nanocrystals bound to the substrate;

(b) exposing the complexes, if formed, in the detection system to a wavelength of light suitable for exciting the functionalized nanocrystals of the complexes to emit a luminescence peak; and (c) detecting the luminescence peak emitted by the complexes, if present, by a detection means for detecting the luminescence peak;

wherein the detection of a luminescence peak is indicative of the presence of the substrate.

37. The method according to claim 36, wherein the presence of the substrate is detected, and further comprises quantitating the amount of substrate present by measuring the intensity of the luminescence peak emitted.

38. The method according to claim 36, wherein the detection system is selected from the group consisting of an affinity assay, fluorescent staining, flow cytometry, nucleic acid sequencing, nucleic acid hybridization, nucleic acid synthesis or amplification, identification verification, and molecular sorting.

39. A method of using the water-soluble, functionalized nanocrystal according to claim 18 in a detection system, the method comprising the steps of:

(a) contacting the functionalized nanocrystals with a sample being analyzed for the presence or absence of a substrate for which the affinity ligand has binding specificity, wherein if the substrate is present in the sample, formed are complexes comprising the functionalized nanocrystals bound to the substrate;

(b) exposing the complexes, if formed, in the detection system to a wavelength of light suitable for exciting the functionalized nanocrystals of the complexes to emit a luminescence peak; and (c) detecting the luminescence peak emitted by the complexes, if present, by a detection means for detecting the luminescence peak;

wherein the detection of a luminescence peak is indicative of the presence of the substrate.

40. The method according to claim 39, wherein the presence of the substrate is detected, further comprising quantitating the amount of substrate present by measuring the intensity of the luminescence peak emitted.

41. The method according to claim 39, wherein the detection system is selected from the group consisting of an affinity assay, fluorescent staining, flow cytometry, nucleic acid sequencing, nucleic acid hybridization, nucleic acid synthesis or amplification, identification verification, and molecular sorting.

42. A method of using the water-soluble, functionalized nanocrystal according to claim 25 in a detection system, the method comprising the steps of:

(a) contacting the functionalized nanocrystals with a sample being analyzed for the presence or absence of a substrate for which the affinity ligand has binding specificity, wherein if the substrate is present in the sample, formed are complexes comprising the functionalized nanocrystals bound to the substrate;

(b) exposing the complexes, if formed, in the detection system to a wavelength of light suitable for exciting the functionalized nanocrystals of the complexes to emit a luminescence peak; and (c) detecting the luminescence peak emitted by the complexes, if present, by a detection means for detecting the luminescence peak;

wherein the detection of a luminescence peak is indicative of the presence of the substrate.

43. The method according to claim 42, wherein the presence of the substrate is detected, further comprising quantitating the amount of substrate present by measuring the intensity of the luminescence peak emitted.

44. The method according to claim 42, wherein the detection system is selected from the group consisting of an affinity assay, fluorescent staining, flow cytometry, nucleic acid sequencing, nucleic acid hybridization, nucleic acid synthesis or amplification, identification verification, and molecular sorting.

45. A method of using the water-soluble, functionalized nanocrystal according to claim 33 in a detection system, the method comprising the steps of:

(a) contacting the functionalized nanocrystals with a sample being analyzed for the presence or absence of a substrate for which the affinity ligand has binding specificity, wherein if the substrate is present in the sample, formed are complexes comprising the functionalized nanocrystals bound to the substrate;

(b) exposing the complexes, if formed, in the detection system to a wavelength of light suitable for exciting the functionalized nanocrystals of the complexes to emit a luminescence peak; and (c) detecting the luminescence peak emitted by the complexes, if present, by a detection means for detecting the luminescence peak;

wherein the detection of a luminescence peak is indicative of the presence of the substrate.

46. The method according to claim 45, wherein the presence of the substrate is detected, further comprising quantitating the amount of substrate present by measuring the intensity of the luminescence peak emitted.

47. The method according to claim 45, wherein the detection system is selected from the group consisting of an affinity assay, fluorescent staining, flow cytometry, nucleic acid sequencing, nucleic acid hybridization, nucleic acid synthesis or amplification, identification verification, and molecular sorting.

* * * * *

UNITED STATES PATENT AND TRADEMARK OFFICE
CERTIFICATE OF CORRECTION

PATENT NO. : 6,114,038                          Page 1 of 1
DATED : September 5, 2000
INVENTOR(S) : Stephanie L. Castro; Emilio Barberá-Guillem.

It is certified that error appears in the above-identified patent and that said Letters Patent is hereby corrected as shown below:

Inventors:
Emilio–Barbera-Guillem; Stephanie L. Castro.

Assignee: Bio-Pixels Ltd.

References Cited:
U.S. PATENT DOCUMENTS
5,751,018       5/1998    Alivisatos et al. ........... 257/64
5,990,479       11/1999   Weiss et al. ............... 250/307

Signed and Sealed this

Twenty-sixth Day of June, 2001

Attest:

NICHOLAS P. GODICI
*Attesting Officer*      *Acting Director of the United States Patent and Trademark Office*